United States Patent [19]

Sato

[11] Patent Number: 4,982,727
[45] Date of Patent: Jan. 8, 1991

[54] ENDOSCOPIC TREATING INSTRUMENT

[75] Inventor: Yukio Sato, Kodaira, Japan

[73] Assignee: Olympus Optical Co., Ltd., Tokyo, Japan

[21] Appl. No.: 509,634

[22] Filed: Apr. 13, 1990

[30] Foreign Application Priority Data

Apr. 13, 1989 [JP] Japan .............................. 1-143272[U]
Sep. 22, 1989 [JP] Japan .................. 1-1247694

[51] Int. Cl.[5] .............................................. A61B 1/00
[52] U.S. Cl. ......................................... 128/4; 606/205
[58] Field of Search ....................... 128/4, 6; 606/205

[56] References Cited

U.S. PATENT DOCUMENTS

| 3,788,304 | 1/1974 | Takahashi | 128/6 |
| 3,895,636 | 7/1975 | Schmidt | 606/205 |
| 4,271,845 | 6/1981 | Chigashige et al. | 128/4 X |
| 4,817,630 | 4/1989 | Schintgen et al. | 128/751 |

FOREIGN PATENT DOCUMENTS

| 8808285 | 9/1988 | Fed. Rep. of Germany . |
| 53-150092 | 11/1978 | Japan . |
| 55-109501 | 7/1980 | Japan . |
| 56-8029 | 1/1981 | Japan . |
| 59-8946 | 1/1984 | Japan . |

Primary Examiner—William H. Grieb

[57] ABSTRACT

An endoscopic treating instrument having a coil sheath, and a treating portion at the distal end of the coil sheath. The coil sheath includes a distal portion having a flexible coil sheath formed by a single wire, a proximal portion having a relatively hard coil sheath formed by a plurality of wires, and an intermediate portion between the distal and proximal portions, the intermediate portion having a coil sheath of an intermediate hardness between the hardness of the coil sheaths of the distal and proximal portions. This structure can prevent the coil sheath from being broken in its intermediate portion.

12 Claims, 6 Drawing Sheets $150 \leq a \leq 300$
$20 \leq b \leq 100$
c: Arbitrary $150 \leq e \leq 300$
$30 \leq f \leq 100$
$30 \leq g \leq 100$
h: Arbitrary

ENDOSCOPIC TREATING INSTRUMENT

BACKGROUND OF THE INVENTION

1. Field of the Invention

This invention relates to an endoscopic treating instrument, more particularly to a coil sheath of an endoscopic treating instrument.

2. Related Art Statement

A conventional treating instrument to be inserted in a forceps channel of an endoscope for making various treatments for internal body tissue comprises, inter alia, a treating portion at the distal end, an operating portion at the proximal end, an operating wire between the operating portion and the treating portion for transmitting the movement of the operating portion to the treating portion at the distal end, and a sheath surrounding the operating wire along its full length.

In order to bend smooth the endoscope in which a treating instrument is inserted, such treating instruments as disclosed in Japanese Laid-Open Patent Applications, Publication Nos. 56-8029 and 59-8946, and Japanese Laid-Open Utility Model Application, Publication No. 53-150092 have been proposed. These prior art publications disclose treating instruments in which the hardness of the sheath is varied in such a manner that the distal end portion is soft so as to be bent and that the other portion is relatively hard.

Further, Japanese Laid-Open Utility Model Application, Publication No. 55-109501 discloses a sheath which comprises a proximal sheath made of a relatively hard coil of a plurality of wires; a distal sheath made of a very flexible coil of a single wire; and a connecting tube connecting the proximal and distal sheaths.

The above-described conventional treating instruments, in which the distal and proximal sheaths having different hardness are connected, have such a drawback as shown in FIG. 1 when they are inserted in a channel of an endoscope. FIG. 1 shows that a treating instrument comprising a soft distal coil sheath 40, a hard coil sheath 41 and a connecting tube 42 connecting both sheaths is broken at the connecting tube 42 where the instrument is weak in rigidity. Consequently, the inner surface of the endoscope channel may be scraped off, and the instrument may be caught in the channel and cannot be drawn out from the endoscope in the worst case.

SUMMARY OF THE INVENTION

An object of the present invention is to provide a safe endoscopic treating instrument the sheath of which cannot be broken in its intermediate portion.

An endoscopic treating instrument according to the present invention comprises a coil sheath, and a treating portion at the distal end of the coil sheath, in which the coil sheath comprises a distal portion having a flexible coil sheath formed by a single wire, a proximal portion having a relatively hard coil sheath formed by a plurality of wires, and an intermediate portion between the distal and proximal portions, the intermediate portion having a coil sheath of an intermediate hardness between the hardness of the coil sheaths of the distal and proximal portions. This structure can prevent the coil sheath from being broken in its intermediate portion.

DETAILED DESCRIPTION OF THE PREFERRED EMBODIMENTS

Figure 1:
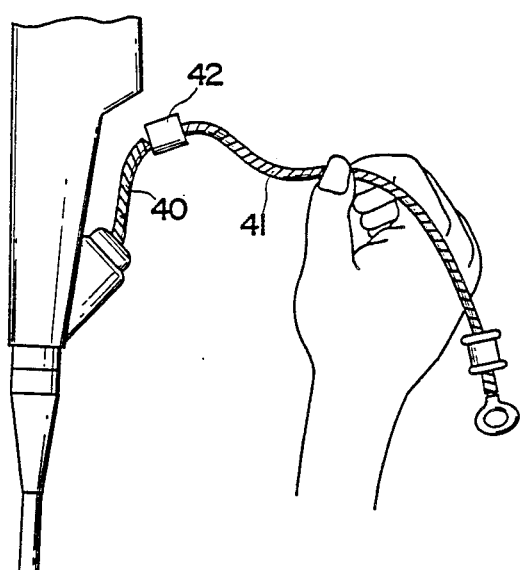
FIG. 1 is an illustration of a drawback of a conventional endoscopic treating instrument.
Figure 2:
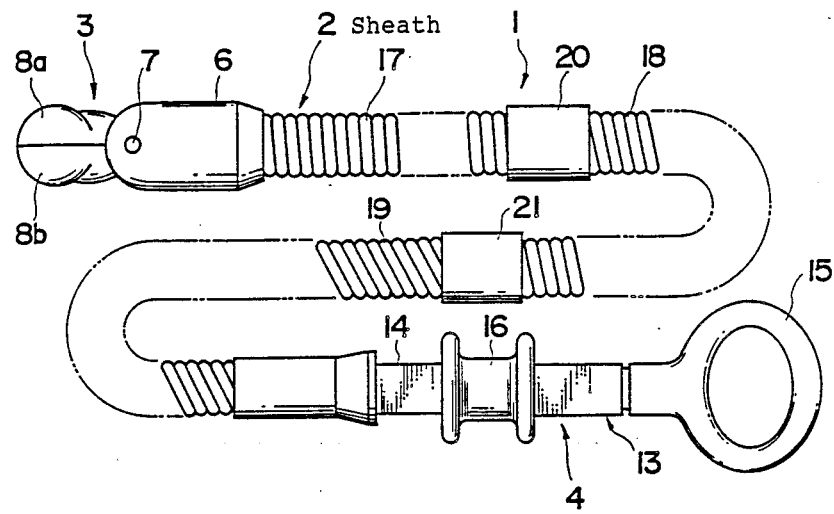
FIG. 2 is a whole view of a treating instrument of a first embodiment of the present invention.

Referring to FIGS. 2 to 7, a first embodiment of the present invention is described.

An endoscopic treating instrument 1 (in this embodiment, a biopsy forceps) comprises a sheath 2 made of a closely wound flexible coil; a treating portion 3 at the distal end of the sheath 2; an operating portion 4 at the proximal end of the sheath 2; and an operating wire 5 inserted in the sheath 2 for transmitting the movement of the operating portion 4 to the treating portion 3.

Figure 3:
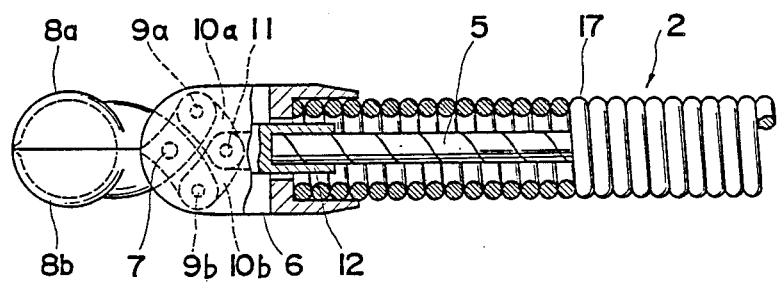
FIG. 3 is a sectional view of the distal end portion of the treating instrument of the first embodiment.

As shown in FIG. 3 in detail, the treating portion 3 comprises a sleeve 6 fixed at the distal end of the sheath 2, and a couple of biopsy cups 8a and 8b protruding from the sleeve 6 and pivotally supported by a pivot pin 7 fixed to the sleeve 6 so that the biopsy cups 8a and 8b can be opened and closed. The bases of the biopsy cups 8a and 8b are secured to one ends of link plates 10a and 10b by pins 9a and 9b, and the other ends of the link plates 10a and 10b are fixed to a coupling member 12 by a pin 11. The coupling member 12 is fixed to the distal end of the operating wire 5 in the sheath 2. Although in the illustrated example the biopsy cups 8a and 8b are used in the treating portion 3, various kinds of forceps, for example, grasping forceps, diathermic snares, diathermic cutters, brushes, etc., may be used.

The operating portion 4 at the proximal end of the sheath 2 includes an operating body 13 fixed at the rear end of the sheath 2, and the operating body 13 comprises a shaft 14 and a thumb ring 15 at the rear end of the shaft 14. A hollow slider 16 is loosely fitted on the shaft 14 and slidable in the axial direction of the shaft 14. The proximal end of the operating wire 5 extending through the sheath 2 is fixed to the sleeve 6.

The sheath 2 surrounding the operating wire 5 comprises three different kinds of closely wound coils: a distal coil 17, an intermediate coil 18 and a proximal coil 19, in the order from the distal treating portion 3. The distal end of the distal coil 17 is fixed to the sleeve 6 of the treating portion 3, and the distal coil 17 and the intermediate coil 18 are fixedly connected by a connecting tube 20. The intermediate coil 18 is fixed to the distal end of the proximal coil 19 by a connecting tube 21, and the proximal end of the proximal coil 19 is fixedly connected to the operating body 13.

The distal coil 17, the intermediate coil 18 and the proximal coil 19 are formed in such a manner that their hardness gradually increases from the distal end: for example, the distal coil 17 is formed by a single, closely wound stainless steel wire, the intermediate coil is made of a single, closely wound stainless steel wire having a diameter larger than that of the distal coil 17, and the proximal coil is formed by a plurality of closely wound stainless steel wires.

Figure 4:
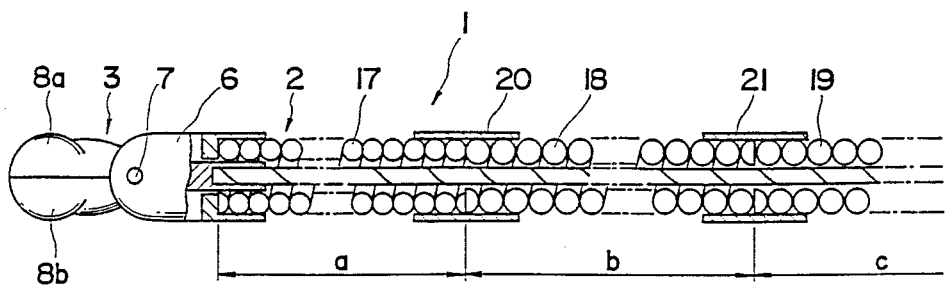
FIG. 4 is a sectional view of the main part of the first embodiment.

As shown in FIG. 4, the distal coil 17 is 150 mm to 300 mm long, the intermediate coil 18 is 20 mm to 100 mm long, and the length of the proximal coil 19 is arbitrary.

Figure 5:
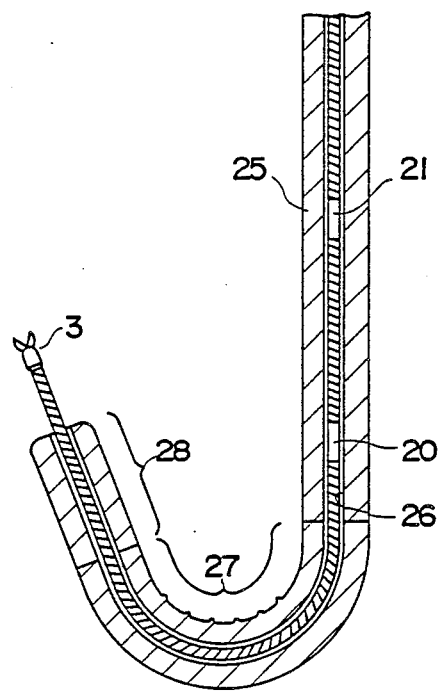
FIG. 5 is a sectional view of the treating instrument of the first embodiment inserted in a channel of an endoscope.
Figure 6:
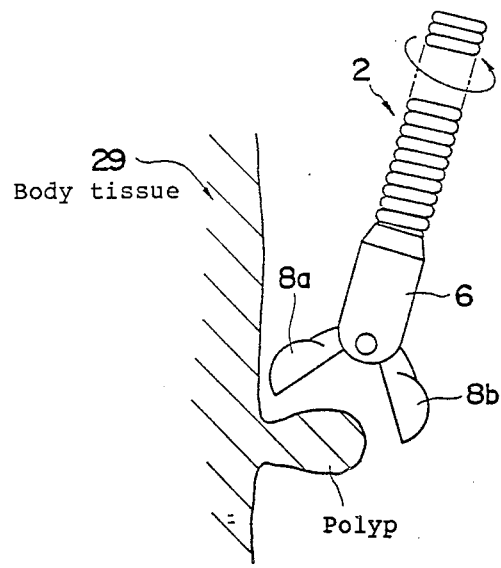
FIGS. 6 and 7 are illustrations showing a way of use of the treating instrument of the first embodiment.
Figure 7:
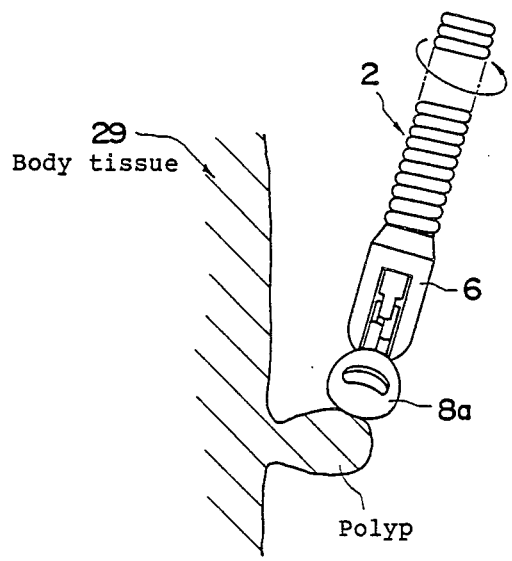

The operation of the treating instrument 1 having the above-described structure is explained. As shown in FIG. 5, the treating instrument 1 is inserted in a forceps channel 26 formed in an endoscope 25, and the treating portion 3 passes through a bending portion 27 of the endoscope and protrudes from a distal end portion 28. Then, an operator inserts his thumb in the thumb ring 15 and holds the slider 16 between his first and middle fingers. When the slider 16 is slid back and forth along the shaft 14 of the operating body 13, the operating wire 5 is pulled or relaxed so that the biopsy cups 8a and 8b of the treating portion 3 are closed or opened via the link mechanism such as the link plates 10a and 10b, etc. That is, when the slider 16 is pulled, the biopsy cups 8a and 8b are closed; when the slider 16 is pushed, the biopsy cups 8a and 8b are opened.

With the above-described structure, when the treating instrument 1 is inserted in the forceps channel 26, the treating portion 3 can be directed to an aimed body part by bending the bending portion 27 and rotated via the sheath 2 by rotating the operating portion 4 of the treating instrument 1. Since the proximal sheath 19 of the sheath 2 is harder than the distal coil 17, the sheath will not be twisted and can surely transmit the rotation of the operating portion 4 to the treating portion. In particular, when the biopsy cups 8a and 8b are open with respect to body tissue 29 in the posture shown in FIG. 6, the biopsy cups 8a and 8b can be rotated via the sheath 2 by rotating the shaft 14 (not shown) to approach the body tissue 29 in the posture shown in FIG. 7, thereby facilitating biopsy.

Further, since the distal coil 17 is the softest among the three coils of the sheath 2, the bending portion 27 of the endoscope can be bent without difficulty.

Moreover, since the intermediate coil 18 is provided between the distal coil 17 and the proximal coil 19 and has an intermediate hardness between that of the distal coil 17 and the proximal coil 19, the hardness of the entire sheath 2 does not vary abruptly so that the sheath 2 will not be broken in its intermediate portion such as the joint with the connecting tube.

Figure 8:
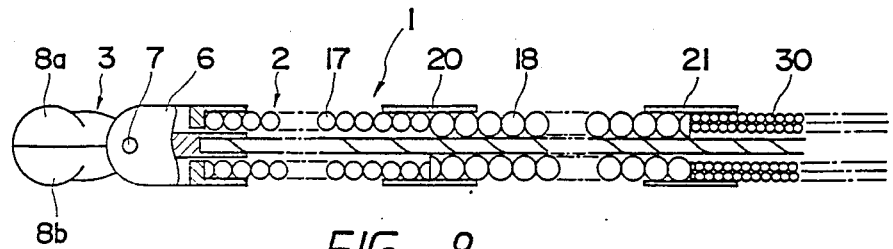
FIG. 8 is a sectional view of the main part of a treating instrument of a second embodiment of the present invention.

Next, FIG. 8 shows a second embodiment of the present invention. The same elements as those of the first embodiment are assigned the same numerals, and their description is omitted.

The second embodiment uses a proximal coil 30 comprising a plurality of overlapping coils each of which is made of a plurality of wires. Its functions and effects are the same as those of the first embodiment.

Figure 9:
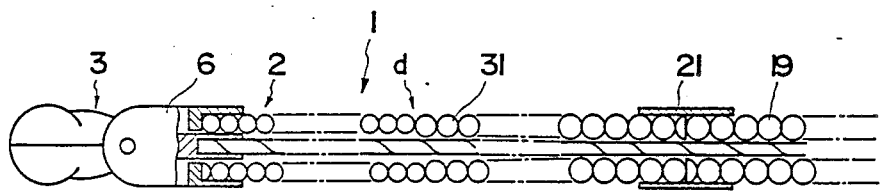
FIG. 9 is a sectional view of the main part of a treating instrument of a third embodiment of the present invention.

FIG. 9 shows a third embodiment of the present invention. In this embodiment, a distal coil 31 is formed by a single wire, the diameter of which is varied at point d. That is, the distal side of the coil 31 with respect to point d is thin and the proximal side is thick.

In this manner, the number of a connecting tubes and the like can be reduced, thereby strengthening the sheath 2.

Figure 10:
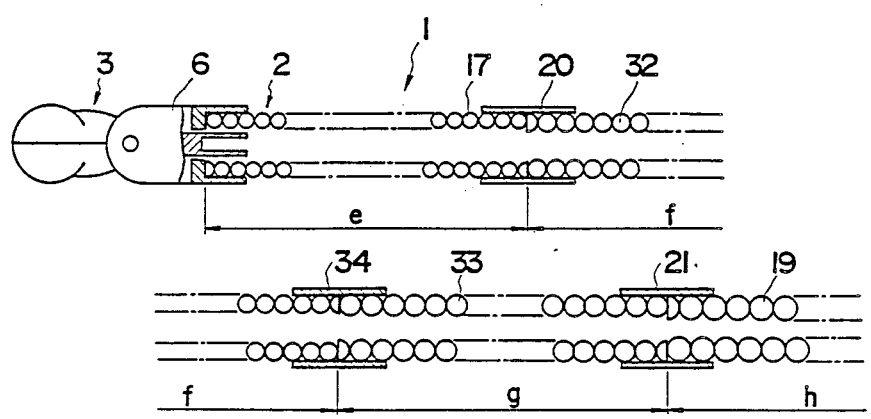
FIG. 10 is a sectional view of the main part of a treating instrument of a fourth embodiment of the present invention.

FIG. 10 shows a fourth embodiment of the present invention. In this embodiment, the coil between a distal coil 17 and a proximal coil 19 is formed by a first intermediate coil 32 and a second intermediate coil 33, which are fixedly connected with each other by a connecting tube 34. The hardness of the coil is varied by making the diameter of the wire of the first intermediate coil 32 small and that of the second intermediate coil 33 large, thereby obtaining a subtle variation of hardness. The distal coil 17 is 150 mm to 300 mm long, the first intermediate coil 32 is 30 mm to 100 mm long, the second intermediate coil 33 is 30 mm to 100 mm long, and the length of the proximal coil 19 is arbitrary.

Experiment

Figure 11:
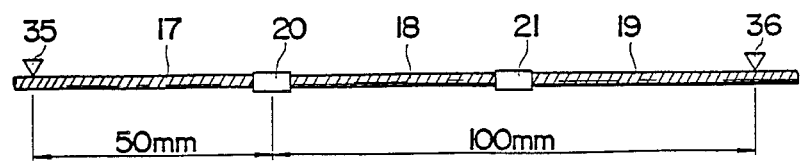
FIGS. 11 and 12 are illustrations of an experiment of the present invention.
Figure 12:
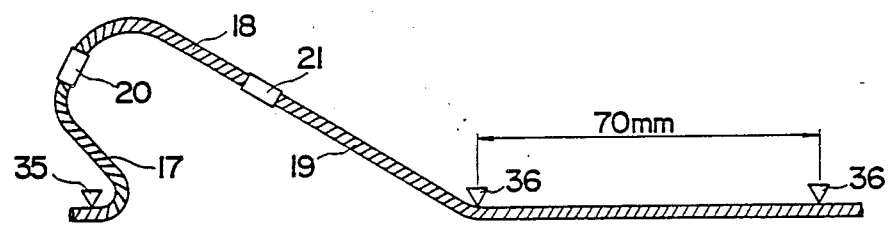

In order to compare an endoscopic treating instrument according to the present invention with a conventional endoscopic treating instrument, an experimental test of the breakage of the sheath was conducted. In an endoscopic treating instrument shown in FIG. 11, a fixed point 35 is positioned on the distal side at a distance of 50 mm from a connecting tube 20, and a held point 36 is positioned on the proximal side at a distance of 100 mm from the connecting tube 20. As shown in FIG. 12, the held point 36 is shifted toward the distal end by 70 mm to bend the instrument to find out whether the sheath is broken.

As a result, in the case of the endoscopic treating instrument according to the present invention its sheath was not broken after it had been bent repeatedly 500 times, while in the case of the conventional treating instrument its sheath was broken after it had been bent repeatedly 100 times.

According to the present invention, the hardness of the sheath is increased gradually from the distal end to the proximal end, thereby preventing the breakage of the sheath at the connecting point.

What is claimed is:

1. An endoscopic treating instrument comprising a coil sheath having a treating portion at a distal end of the coil sheath, the coil sheath comprising:
   a distal coil portion formed by a single wire,
   a proximal coil portion formed by a plurality of wires, the proximal coil portion being harder than the distal coil portion, and
   an intermediate coil portion between the distal and proximal coil portions, the intermediate coil portion being of an intermediate hardness between the hardness of the distal and proximal coil portions.

2. The endoscopic treating instrument of claim 1, in which the intermediate coil portion is formed by a single wire of a diameter larger than the wire of the distal coil portion.

3. The endoscopic treating instrument of claim 2, in which the distal coil portion is formed by a single stainless steel wire and the proximal coil portion is formed by a plurality of stainless steel wires.

4. The endoscopic treating instrument of claim 1, in which the proximal coil portion is formed by a plurality of overlapping coils, each of which is formed buy a plurality of stainless steel wires.

5. The endoscopic treating instrument of claim 4, in which the distal coil portion is formed by a single stainless steel wire and the intermediate coil portion is formed by a single wire of a diameter larger than the wire of the distal coil portion.

6. The endoscopic treating instrument of claim 1, 2, 3, 4 or 5, in which the distal, intermediate and proximal coil portions are connected by connecting tubes.

7. The endoscopic treating instrument of claim 1, in which the distal and intermediate coil portions are formed by a common wire.

8. The endoscopic treating instrument of claim 1, in which the intermediate coil portion further comprises a soft distal portion and a hard proximal portion.

9. The endoscopic treating instrument of claim 1, in which the treating instrument is adapted to be inserted in a channel of an endoscope to be introduced into a body cavity.

10. The endoscopic treating instrument of claim 9, in which the distal coil portion is adapted to be positioned in a bending portion of an endoscope when the endoscopic treating instrument is inserted in a channel of the endoscope.

11. An endoscopic treating instrument comprising a coil sheath having a distal end and a proximal end; a treating portion at the distal end of the coil sheath; and an operating portion at the proximal end of the coil sheath, the coil sheath comprising:
 a distal coil portion formed by a single wire,
 a proximal coil portion having a relatively hard coil sheath formed by a plurality of wires, and
 an intermediate coil portion between the distal and proximal coil portions, the intermediate coil portion having a coil sheath of an intermediate hardness between the hardness of the coil sheaths of the distal and proximal portions.

12. The endoscopic treating instrument of claim 11, in which the treating and operating portions are connected by an operating wire disposed in the coil sheath.

* * * * *